United States Patent [19]

Zamba et al.

[11] Patent Number: 4,606,342
[45] Date of Patent: Aug. 19, 1986

[54] CAUTERY DEVICE HAVING A VARIABLE TEMPERATURE CAUTERY TIP

[75] Inventors: Eugene Zamba; Lynan Zamba, both of Brooklyn, Conn.

[73] Assignee: National Patent Development Corporation, New York, N.Y.

[21] Appl. No.: 702,119

[22] Filed: Feb. 15, 1985

[51] Int. Cl.$^4$ .............................................. A61B 17/36
[52] U.S. Cl. ................................................ 128/303.17
[58] Field of Search ...................... 128/303.17–303.19, 128/303.13–303.14, 303.1, 783, 800–807

[56] References Cited

U.S. PATENT DOCUMENTS

| | | | |
|---|---|---|---|
| 1,401,104 | 12/1921 | Kreusheld et al. | 128/303.14 |
| 1,677,209 | 7/1928 | Rose | 128/303.14 |
| 1,812,608 | 6/1931 | Roberts | 128/303.14 |
| 2,376,265 | 5/1945 | Merebith | 128/303.14 |
| 3,720,896 | 3/1973 | Beierlein | 128/303.17 |
| 3,978,312 | 8/1976 | Barton et al. | 128/303.14 |

FOREIGN PATENT DOCUMENTS 2504508  8/1976  Fed. Rep. of Germany ........................ 128/303.17

Primary Examiner—William E. Kamm
Attorney, Agent, or Firm—Vincent P. Pirri

[57] ABSTRACT

A portable cauterizing device having a variable temperature cautery tip that is activated by switching means that also performs the additional function of varying the temperature of the cautery tip so that the device can be activated and the temperature of the cautery tip can be regulated using only one hand.

10 Claims, 12 Drawing Figures

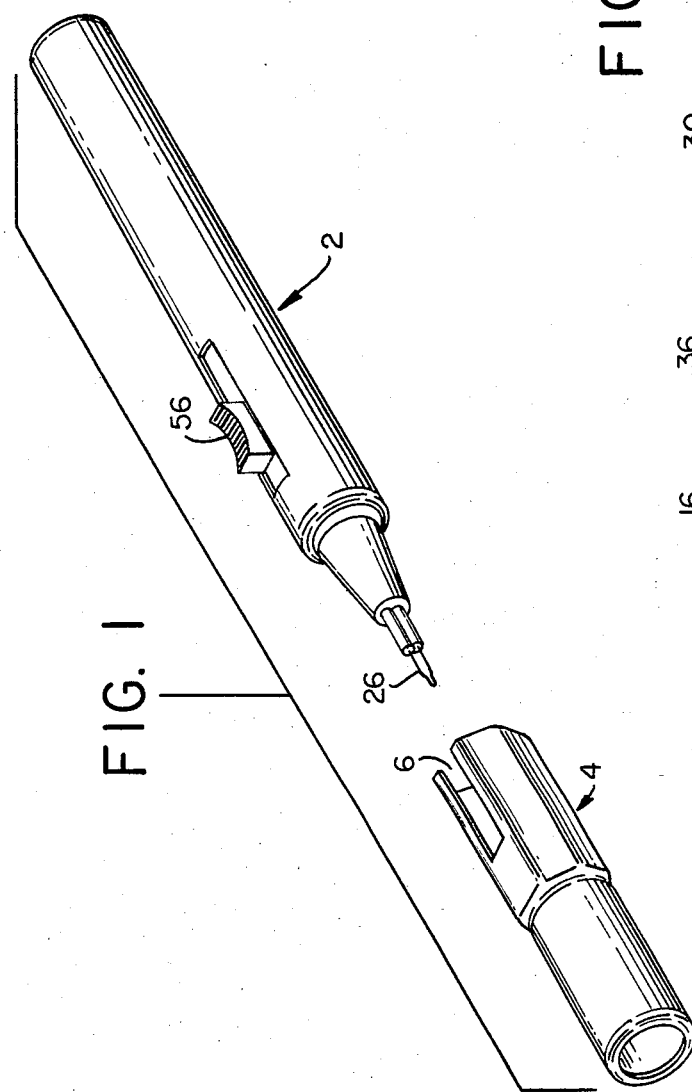
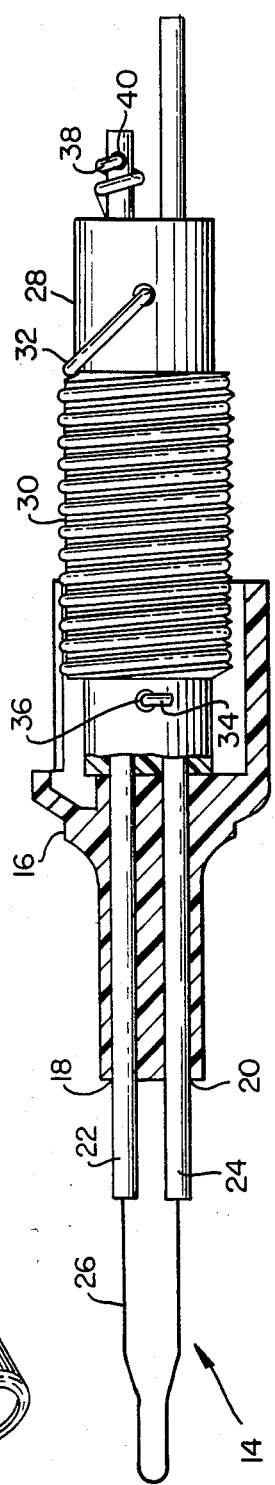

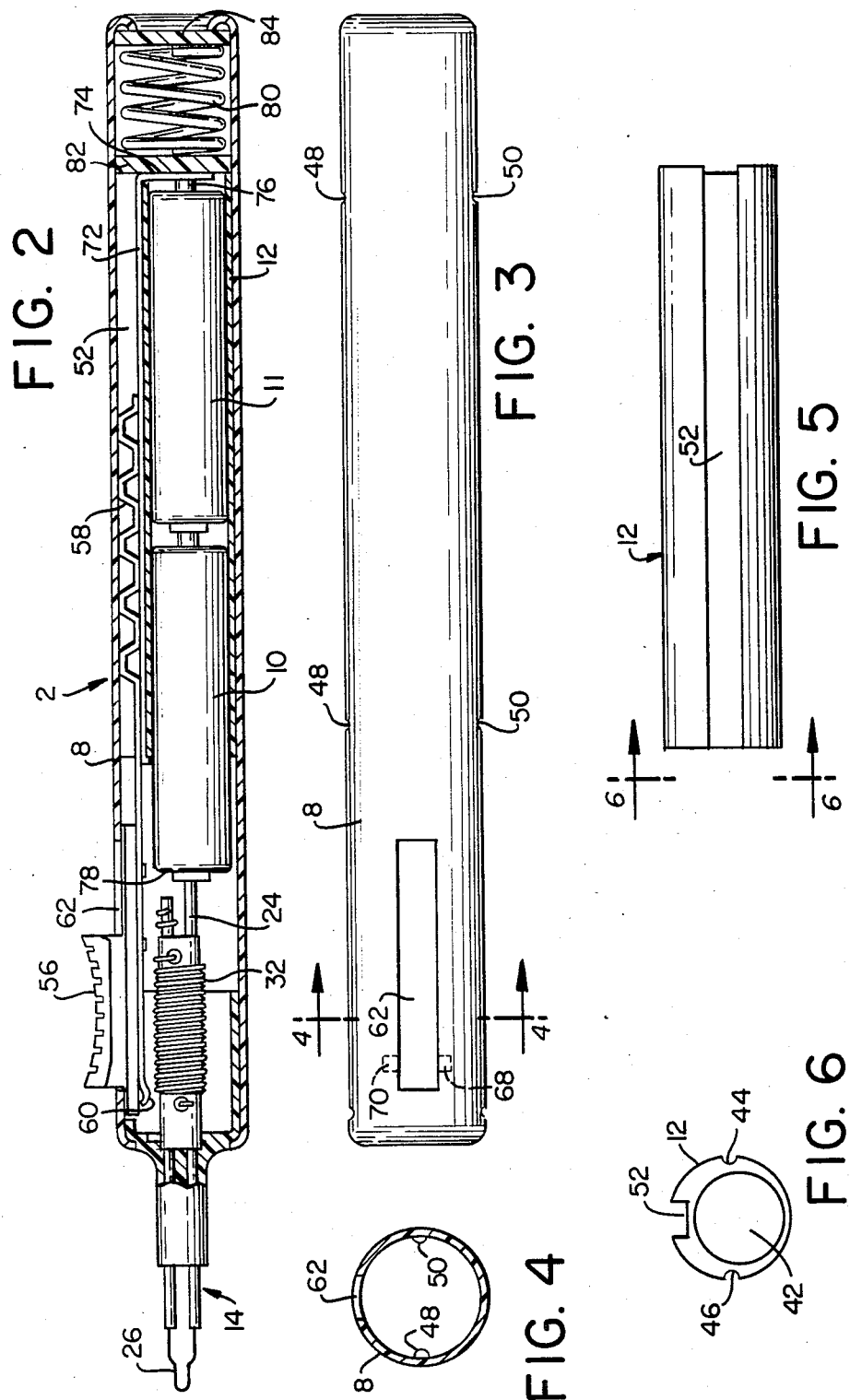

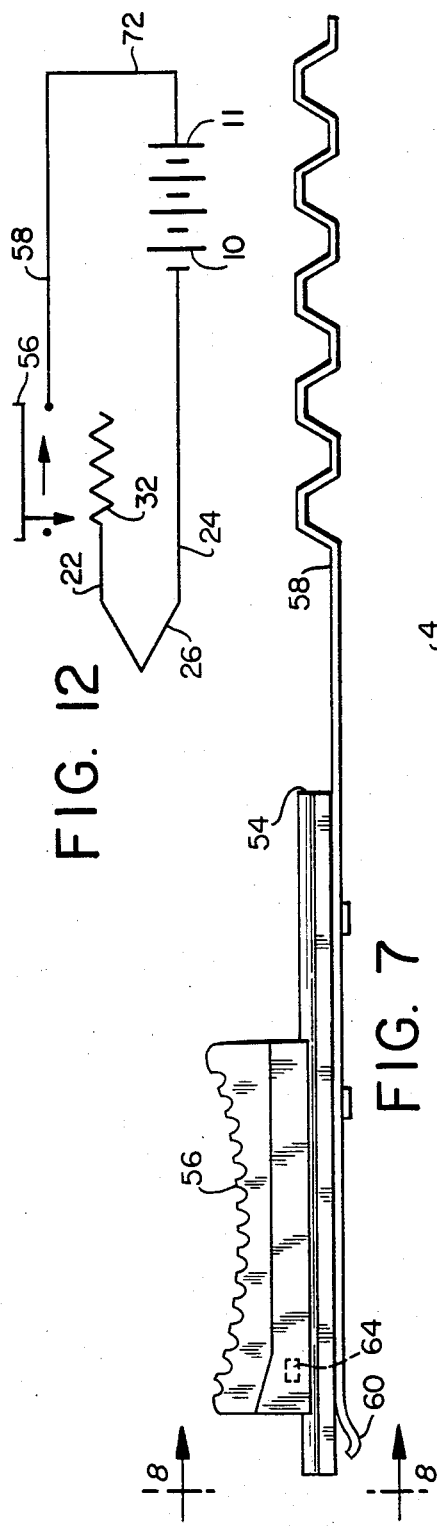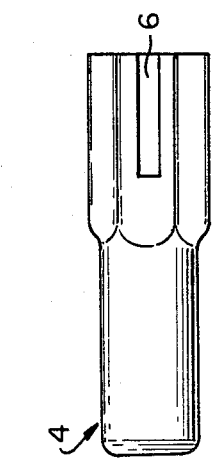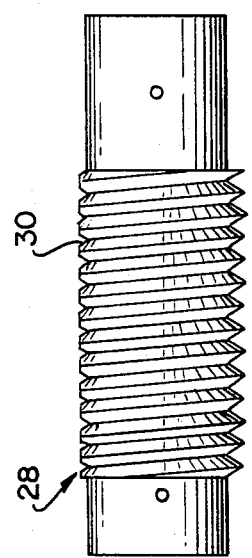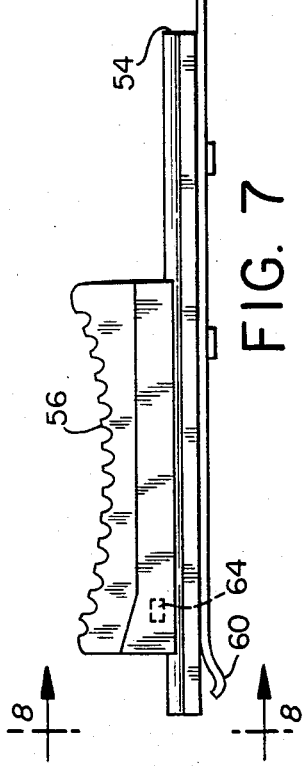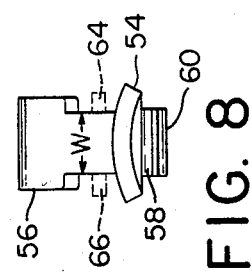

CAUTERY DEVICE HAVING A VARIABLE TEMPERATURE CAUTERY TIP

DESCRIPTION

1. Technical Field

The invention relates to a cauterizing device having a cautery tip in which the actuator means for the device can also be used to vary the power fed to the cautery tip and thereby vary the temperature of the cautery tip.

2. Background of the Invention

There are many cautery devices disclosed in the art which use hot-wire cauteries designed for use in surgical operations or procedures ranging from simple surgical procedures performed in a doctor's office to complex operations performed in hospital operating rooms by surgeons. Specifically, in many surgical procedures, the surgeon is required to apply localized heat to a localized portion of the body (blood vessel) to effectively coagulate the blood and thereby control the amount of bleeding. Cautery devices have been used to pinpoint hemostasis in ophthalmic and other microsurgical procedures, to effectively coagulate the vas deferens and control the amount of bleeding in the surrounding tissues, to pinpoint hemostasis of bleeding points encountered in skin and subcutaneous tissue, and to coagulate bleeding in recessed areas such as encountered during oral and nasal surgery. Cautery devices have also been used for parting sutures. However, each surgery procedure usually requires a specific temperature for coagulation and therefore fixed temperature cautery hot-wire devices has been extensively used.

U.S. Pat. No. 3,978,312 discloses a variable temperature portable cautery includes a housing configured to retain a voltage source, such as a plurality of batteries, and an electrically heated cautery tip carried by the front end of the housing in operative relation with each other. A manually operable switch is provided on the housing to allow selective energization of the cautery tip from the voltage source. A rotatably adjustable variable resistor is mounted on the rear end of the housing and is connected in circuit between the voltage source and heated tip to allow the temperature of the tip to be selectively varied. The movable contact of the switch and the wiper contact of the variable resistor are provided by the respective ends of a common conductor member extending longitudinally in the housing.

The disadvantage of this type of cautery device is that it requires one manually operative switch mounted on the side of the device to energize the cautery tip and a second manually operative, rotatable switch mounted on the end of the device to adjust the resistance of the resistor in the circuit so as to adjust the temperatures of the cautery tip. Consequently, this device requires the operation of two separate switching means before the device can be employed. Specifically, the rotary switching means has to be operated to give a desired cautery tip temperature and then the second switching means has to be activated to connect the power or voltage source across the cautery tip. Once the desired temperature of the cautery tip is fixed, the doctor proceeds with the surgical operation and merely has to activate the switch to heat the cautery tip. However, if the temperature of the cautery tip is found to be too low or too high for the particular surgical procedure, the doctor will have to remove the device from the operating area in order to adjust the rotary switch at the end of the device. This procedure of varying the temperature of the cautery tip by a separate rotary switch will require the use of both hands of the doctor and therefore could prove to be quite inefficient during a cauterizing procedure. This is particularly true in micro surgery where the surgeon works under a microscope since the cauterizing would have to be stopped if the temperature of the cautery tip is found to be wrong for the procedure. The device would have to be removed from under the microscope and then be re-adjusted to the right temperature before the procedure could be continued.

OBJECTS OF THE INVENTION

Accordingly, one or more objects will be achieved in the practice of the invention.

Objects for the invention are for the provisions of novel cautery devices having a single switching means for activating the device and varying the temperature of the cautery tip.

Another object of the invention is to provide a portable variable temperature cautery device that can be operated by one hand to both activate the device and vary the temperature of the cautery tip of the device.

Yet another object of the invention is to provide a portable cautery device employing a cautery tip that can be varied over a temperature from 0° F. up to about 2200° F.

Still another object of the invention is to provide a variable temperature cautery device that is not labor intensive to assemble or capital intensive to produce.

The foregoing as well as additional objects will become fully apparent from the following description and the accompanying drawing.

DISCLOSURE OF THE INVENTION

The invention relates to a variable temperature cauterizing device comprising a housing containing power supply means having a first terminal and a second terminal; an electrically heatable cautery tip extending from said housing and having a first terminal means and a second terminal means, said first terminal means electrically connected to the first terminal of said power supply means; a resistive element electrically connected to the second terminal means of said cautery tip; a conductor means having a first end and a second end, said first end electrically connected to the second terminal of said power supply means; a moveable activator means having a first end and a second end, said first end electrically connected to the second end of said conductor means and said second end adapted to electrically contact and slide along said resistive element so that when said activator means contacts said resistive element a complete circuit is produced in which the power supply means will be applied to the cautery tip and when the activator means is slid along said resistive element the power applied to the cautery tip will vary thereby varying the temperature of said cautery tip.

The resistive element for use in this invention can be of the conventional type in which the resistance is proportion to the length of the resistive element. For example, a rheostat can be employed which consists of a coil of resistance wire wound closely on a cylindrical insulator so that the terminal end of the activator can bear upon and slide on the wires themselves so as to eliminate any desired number of turns of the resistance wire. Thus by varying the resistance in the circuit, the power fed to the cautery tip can be varied thereby varying the temperature of the cautery tip. For most applications, the variable resistor should be selected so that the temperature of the cautery tip can vary from 0° F. up to about 2200° F. and preferably from about 100° F. up to about 1800° F.

The activator means could be designed so that it will require a constant force to maintain contact with the resistive element or could be designed so that once the activator means contacts the resistive element at a specific location on the resistive element, the activator means will maintain contact with the resistive element without the need for applying a constant external force. In the former embodiment, the user would have to maintain pressure on the activator means at all times to maintain the power supply means coupled to the cautery tip. In the latter embodiment, once pressure is applied to the activator means to contact the resistive element, the external pressure can be removed and the activator means will be maintained bias against the resistive element. In either embodiment, the user will be able to change the temperature of the cautery tip by simply sliding the activator means along the resistive element.

BRIEF DESCRIPTION OF THE DRAWINGS

The present invention will become more apparent from the following description thereof when considered together with the accompanying drawing which is set forth as being exemplary of embodiments of the present invention and is not intended in any way to be limited thereof and wherein:

FIG. 1 is a perspective view shown a protective cap detached from a variable temperature cautery device of this invention.

FIG. 2 is a side elevation in cross-section of the variable cautery device shown in FIG. 1.

FIG. 3 is a plan view of the housing of the variable cautery device shown in FIG. 2.

FIG. 4 is a view taken along line 4—4 of FIG. 3.

FIG. 5 is a plan view of the battery housing for use in the variable cautery device shown in FIG. 2.

FIG. 6 is a view taken along line 6—6 of FIG. 5.

FIG. 7 is a side elevation of the activator means of the variable cautery device of FIG. 2.

FIG. 8 is a view taken along line 7—7 of FIG. 7.

FIG. 9 is a side elevation of the insulator support means for the variable resistor.

FIG. 10 is a side elevation, partly a cross-section, of the cautery tip assembly with the variable resistor mounted in place.

FIG. 11 is a side elevation of the protective cap of the cautery device.

FIG. 12 is a schematic circuit of the cautery device shown in FIG. 2.

DETAILED DESCRIPTION OF DRAWING

FIG. 1 shown a perspective view of a fully assembled cautery device 2 detached from a protective cap 4. As shown in FIGS. 1 and 11, protective cap 4 is designed with an elongated slot 6 to accommodate the projected switch member 56 of the cautery device 2 when said projected cap is secured onto and over the front of the cautery device 2 to protect the cautery tip 26.

As shown in FIG. 2, cautery device 2 comprises a housing 8 containing two series connected batteries 10 and 11 secured within a battery container 12 and having one terminal electrically connected to one terminal of the cautery tip assembly 14. The cautery tip assembly 14 is shown in FIG. 10 comprising a support housing 16 having two circular channels 18 and 20 for accommodating electrical terminals 22 and 24, respectively. Electrically connected and secured to one end of electrical terminals 22 and 24 is a cautery tip or hot wire 26. Mounted on support housing 16 and about the opposite ends of electrical terminals 22 and 24 is a cylindrical insulator 28 having a spiral groove 30 on its exterior surface as shown in FIG. 9. A resistive element 32 is wrapped around and into the spiral groove 30 of insulator 28. One end 34 of resistive element 32 is secured within an opening 36 of insulator member 28 with the opposite end 38 secured within an opening 40 in electrical terminal 22. As evident from FIG. 10, the resistance of the resistive element 32 will depend upon the length of the resistor 32 coupled into a circuit, said length being proportional to the number of turns of the wire on insulator member 28.

FIGS. 5 and 6 shows the cylindrical battery housing 12 having an internal channel 42 to accommodate batteries 10 and 11 as shown in FIG. 2. Two elongation grooves 44 and 46 one disposed 180° apart on the other surface of housing 12 and are designed to mate with two semi-circular projection 48 and 50 disposed 180° apart on the inner wall of housing 8 as shown in FIGS. 3 and 4. This will insure that before battery housing 12 is slide into housing 8, it will have to be properly orientated so that the elongated rectangular groove 52 of battery housing 12 will always be properly orientated within housing 8.

FIGS. 7 and 8 show the activator means for the cautery device which comprises an arcuate insulator mounting support 54 having secured on its top surface a knurled finger gripping member 56 and having secured on its under surface an elongated conductive terminal strip 58. The width of conductive terminal strips 58 is equal to or less than the width of the rectangular groove 52 on battery housing 12 so that one end of strips 58 can slide in groove 52. The opposite end of strips 58 have a V-shaped tip 60 so that when member 56 is depressed, the extermity of V-shaped tip 60 can contact the resistive element 32 as shown in FIG. 2.

As shown in FIG. 3, housing 8 has an elongated slot 62 having a width sufficient to accommodate the width W of knurled finger gripping member 56 so that member 56 can longitudinally slide in slot 62 as shown in FIG. 2. In the embodiment shown in FIG. 2, a depression of member 56 will cause tip 60 of conductive strip 58 to contact resistive element 32 and then by simply sliding member 56 along resistive element 32, the resistance (number of turns of the wire coiled on insulator 28) can be adjusted in the circuit so as to vary the temperature of the cautery tip 26 as will be discussed below. Upon release of external pressure on member 56, the V-shaped tip 60 will be biased away from and break contact with the resistive element 32. An optional embodiment of the activator means would be to mold projections 64 and 66 into the side of knurled finger gripping member 56 as shown in broken lines in FIGS. 7 and 8. These projections 64 and 66 should be made of a size such that they would pass through openings 68 and 70, respectively, defined in housing 8 as shown in FIG. 3. In this embodiment, when member 56 is depressed such that projections 64 and 66 pass through openings 68 and 70, respectively, and then axially slid along resistive element 32, the projections 64 and 66 will be trapped under slot 62 so as to maintain tip 60 in contact with resistive element 32 even when external pressure is released from member 56. Consequently, in the first embodiment pressure will have to be maintained on the member 56 to keep tip 60 in contact with the resistive element 32 while in the second embodiment, the projectors 64 and 66 can be used to maintain tip 60 in contact against resistive element 32.

As shown in FIG. 2 elongated L-shaped conductive terminal 72 is disposed in housing 8 such that the width of terminal 72 is sufficient to seat in elongated groove 52 of battery housing 12 with the tip portion 74 disposed to contact terminal 76 of battery 11. The opposite terminal 78 of battery 10 is disposed to contact terminal 24 of cautery tip assembly 14. A biasing spring 80 is disposed between insulating disc 82 and disc 84 to apply a pressure against terminal 72 to insure good electrical contact between said terminal 72 and terminal 76 of battery 11, and between terminal 78 of battery 10 and terminal 24 of cautery tip assembly 14. To insure good electrical contact between terminal 58 and terminal 72, the end of terminal 58 is corrugated to exert sufficient pressure against terminal 72 while still allowing terminal 58 to slide on terminal 72.

A schematic of the electric circuit of the cautery device is shown in FIG. 12 in which one terminal of the series connected batteries 10 and 11 is electrically coupled to terminal 72 which in turn is electrically coupled to terminal 58 of activator member 56. The opposite terminal of series connected batteries 10 and 11 is coupled to terminal 24 of cautery tip 26 while the opposite end of cautery tip 26 is electrically coupled to terminal 22 which in turn is electrically coupled to resistive element 32. As shown in the schematic circuit, a depression of member 56 will cause terminal 58 to contact resistive element 32 thereby completing the circuit and placing the battery source across the cautery tip 26. By simply sliding member 56 across resistive element 32, the resistance in the circuit can be varied in turn will vary the power supplied to the cautery tip 26. By vary the power supplied across the cautery tip 26, the temperature of the cautery tip 26 can be varied to any desirable temperature.

As shown in FIGS. 1 and 2, the cautery device of this invention is operated by removing the protective cap 4 to expose the cautery tip 26. The knurled finger gripping member 56 is depressed to complete the circuit and then slid axially to the rear to place a selected resistance from resistive element 32 into the circuit which will provide a desired voltage to the cautery tip 26 to cause the cautery tip 26 to heat to a desired temperature. If the temperature of the cautery tip 26 is either too high or too low, it can be varied by simply sliding member 56 axially to the front or rear, respectively, of the device. Thus the cautery device of this invention can be operated by one hand to both activate the device and vary the temperature of the cautery tip using one single activation means.

As will be apparent to one skilled in the art, various modifications can be made in the hereinbefore described variable temperature cautery device. The preferred embodiment described are not to be construed as a limitation of the invention.

What is claimed is:

1. A variable temperature cauterizing device comprising a housing containing power supply means having a first terminal and a second terminal; an electrically heatable cautery tip extending from said housing and having a first terminal means and a second terminal means, said first terminal means electrically connected to the first terminal of said power supply means; a resistive element electrically connected to the second terminal means of said cautery tip; a conductor means having a first end and a second end, said first end electrically connected to the second terminal of said power supply means; a moveable activator means having a first end and a second end, said first end electrically connected to the second end of said conductor means and said second end moveable from a first position where it is not in contact with the resistive element to a second position where it contacts the resistive element and is slidable upon said resistive element so that when said activator means is in the second position to contact said resistive element a complete circuit is produced in which the power supply means will be applied to the cautery tip and when the activator means is slid along said resistive element the power applied to the cautery tip will change so as to vary the power fed to the cautery tip and thereby vary the temperature of said cautery tip.

2. The variable temperature cauterizing device of claim 1 wherein the temperature of the cautery tip can vary up to about 2200° F.

3. The variable temperature cauterizing device of claim 2 wherein the temperature of the cautery tip is variable between about 100° F. and about 1800° F.

4. The variable temperature cauterizing device of claim 1 having means for maintaining said second end of said activator means in contact with said resistive element without applying a constant external pressure.

5. The variable temperature cauterizing device of claim 4 wherein the temperature of the cautery tip is variable between about 100° F. and about 2200° F.

6. The variable temperature cauterizing device of claim 1 wherein the resistive element comprises a cylindrical insulator having a resistance wire coiled about said cylindrical insulator.

7. The variable temperature cauterizing device of claim 6 wherein said activator means is moveable to said second position to contact and slide upon the resistance wire coiled about said cylindrical insulator so as to change any desired number of turns of the resistance wire in the circuit of the device.

8. The variable temperature cauterizing device of claim 7 wherein the temperature of the cautery tip is variable between about 100° F. and about 2200° F.

9. The variable temperature cauterizing device of claim 7 having means for maintaining said second end of said activator means in contact with said resistive element without applying a constant external pressure.

10. The variable temperature cauterizing device of claim 9 wherein the temperature of the cautery tip is variable between about 100° F. and about 2200° F.

* * * * *